United States Patent [19]

Mylari et al.

[11] Patent Number: 4,996,204
[45] Date of Patent: Feb. 26, 1991

[54] PYRIDO[2,3-D]PYRIDAZINONES AS ALOOSE REDUCTASE INHIBITORS

[75] Inventors: Banavara L. Mylari, Waterford; William J. Zembrowski, Oakdale, both of Conn.

[73] Assignee: Pfizer Inc., New York, N.Y.

[21] Appl. No.: 350,417

[22] Filed: May 11, 1989

[51] Int. Cl.$^5$ .................. A61K 31/50; C07D 471/04
[52] U.S. Cl. .................................... 514/248; 544/236; 546/116
[58] Field of Search ................. 514/248; 544/236, 237

[56] References Cited

U.S. PATENT DOCUMENTS

| | | | |
|---|---|---|---|
| 3,821,383 | 6/1974 | Sestanj et al. | 424/258 |
| 4,209,527 | 6/1980 | Sarges | 424/273 |
| 4,251,528 | 2/1981 | Brittain et al. | 424/250 |

OTHER PUBLICATIONS

Mylari et al., Chemical Abstracts, vol. 107, No. 176055 (1987) (Abstract for EP No. 222576, 5/20/87).

Ormaza, Chemical Abstracts, vol. 106, No. 67338 (1987)(Abstract for ES No. 548146, 3/16/86).

*Primary Examiner*—Mukund J. Shah
*Assistant Examiner*—E. Bernjardt
*Attorney, Agent, or Firm*—Peter C. Richardson; Paul H. Ginsburg

[57] ABSTRACT

A series of novel 6-substituted-5-oxo-6H-pyrido[2,3-d]pyridazine-8-ylacetic acid and 7-substituted-8-oxo-7H-pyrido[2,3-d]pyridazine-5-ylacetic acid compounds have been prepared, including their $C_1$–$C_6$ alkyl ester derivatives, as well as the base salts of said acids with pharmacologically acceptable cations. Typical member compounds include those acids wherein the ring substitutent is always attached to the available ring-nitrogen atom and is either a lower aralkyl group or a lower heteroaralkyl group. These compounds are useful in therapy as aldose reductase inhibitors for the control of certain chronic diabetic complications. Methods for preparing these compounds from known starting materials are provided.

22 Claims, No Drawings

PYRIDO[2,3-D]PYRIDAZINONES AS ALOOSE REDUCTASE INHIBITORS

BACKGROUND OF THE INVENTION

This invention relates to new pyridazinone derivatives. More particularly, it is concerned with a novel series of pyrido-pyridazinone acetic acid compounds. These compounds are useful in the control of certain chronic complications arising from diabetes mellitus (e.g., diabetic cataracts, retinopathy, nephropathy and neuropathy).

Past attempts to obtain new and better oral antidiabetic agents have, for the most part, involved an endeavor to synthesize new compounds that lower blood sugar levels. More recently, several studies have been conducted concerning the effect of various organic compounds in preventing or arresting certain chronic complications of diabetes, such as diabetic cataracts, nephropathy, neuropathy and retinopathy, etc. For instance, K. Sestanj et al. in U.S. Pat. No. 3,821,383 disclose that certain aldose reductase inhibitors like 1,3-dioxo-1H-benz[d,e]isoquinoline-2(3H)-acetic acid and some closely-related derivatives thereof are useful for these purposes even though they are not known to be hypoglycemic. Additionally, D. R. Brittain et al. in U.S. Pat. No. 4,251,528 disclose various aromatic carbocyclic oxophthalazinyl acetic acid compounds, which are reported to possess useful aldose reductase inhibitory properties. These compounds all function by inhibiting the activity of the enzyme aldose reductase, which is primarily responsible for catalyzing the reduction of aldoses (like glucose and galactose) to the corresponding polyols (such as sorbitol and galactitol) in the human body. In this way, unwanted accumulations of galactitol in the lens of galactosemic subjects and of sorbitol in the lens, retina, peripheral nervous system and kidney of diabetic subjects are prevented or reduced. As a result, these compounds control certain chronic diabetic complications, including those of an ocular nature, since it is already known in the art that the presence of polyols in the lens of the eye leads to cataract formation and concomitant loss of lens clarity.

SUMMARY OF THE INVENTION

The present invention relates to novel pyrido-pyridazinone acetic acid compounds useful as aldose reductase inhibitors for the control of certain chronic complications arising in a diabetic subject. More specifically, the novel compounds of this invention are selected from the group consisting of 6-substituted-5-oxo-6H-pyrido[2,3-d]pyridazine-8-ylacetic acids and 7-substituted-8-oxo-7H-pyrido[2,3-d]pyridazine-5-ylacetic acids of the formulae:

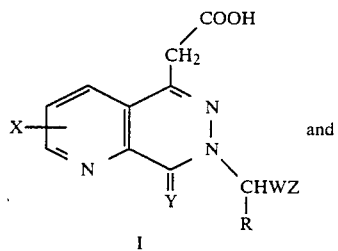

I and

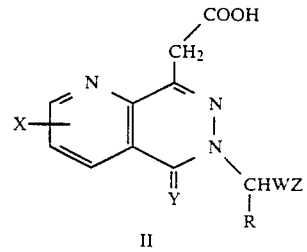

II and the $C_1$–$C_6$ alkyl ester derivatives thereof, and the base salts of said acids with pharmacologically acceptable cations, wherein R is hydrogen or methyl; W is —$(CH_2)_n$— wherein n is zero or one; or R and W, when taken together with the central carbon atom to which they are attached to form RCHW, complete a vinyl group; X is hydrogen, fluorine, chlorine, bromine, trifluoromethyl, $C_1$–$C_4$ alkyl, $C_1$–$C_4$ alkoxy or $C_1$–$C_4$ alkylthio; Y is oxygen or sulfur; and Z is phenyl, thiazolophenyl, trifluoromethylthiazolophenyl, benzothiophenyl, benzoxazolyl, benzothiazolyl, phenyloxadiazolyl, thiazolopyridinyl, oxazolopyridinyl, imidazopyridinyl, triazolopyridinyl or indolyl, wherein said phenyl, benzothiophenyl, benzoxazolyl, benzothiazolyl and phenyloxadiazole groups are each optionally substituted with up to two identical or non-identical substituents on the benzene ring, said identical substituents being fluorine, chlorine, bromine, trifluoromethyl, $C_1$–$C_4$ alkyl or $C_1$–$C_4$ alkoxy and said non-identical substituents being fluorine, chlorine, bromine, trifluoromethyl, methyl, methoxy or hydroxy. These novel compounds are aldose reductase inhibitors and therefore, possess the ability to reduce or inhibit sorbitol formation in the lens and peripheral nerve of diabetic subjects.

One group of compounds of the present invention is that of formula I wherein Z is phenyl, benzothiophen-2-yl, benzoxazol-2-yl, benzothiazol-2-yl or phenyl-1,2,4-oxadiazol-2-yl, including their benzene ring-substituted derivatives as well as their $C_1$–$C_6$ lower alkyl esters. Preferred compounds within this group include those acids wherein R and X are each hydrogen, Y is oxygen, W is —$(CH_2)_n$— wherein n is zero and Z is ring-substituted phenyl, and also including their tertiary-butyl esters, which are of additional value as intermediates leading to the production of the aforesaid acids in a manner that will hereinafter be described.

Another group of compounds of the present invention of interest is that of formula II wherein Z is phenyl, benzothiophen-2-yl, benzoxazol-2-yl, benzothiazol-2-yl or phenyl-1,2,4-oxadiazol-3-yl, including their benzene ring-substituted derivatives as well as their $C_1$–$C_6$ alkyl esters. Preferred compounds within this group include those wherein R and X are each hydrogen, Y is oxygen, W is —$(CH_2)_n$— wherein n is zero and Z is ring-substituted phenyl and also including their tertiary-butyl esters, which are of additional value as intermediates leading to the production of the aforesaid acids in a manner that will hereinafter be described.

Of especial interest are such typical and preferred member compounds of the invention as 6-(5-trifluoromethylbenzothiazole-2-ylmethyl)-5-oxo -6H-pyrido[2,3-d]pyridazine-8-ylacetic acid, 6-(5-fluorobenzothiazole-2-ylmethyl)-5-oxo-6H-pyrido[2,3-d]pyridazine-8-ylacetic acid, 6-[5-(2-trifluoromethylphenyl)-1,2,4-oxdiazole-3-ylmethyl]-5-oxo-6H -pyrido[2,3-d]pyridazine-8-ylacetic acid and 6-(4-bromo-2- fluorobenzyl)-5-oxo-6H-pyrido[2,3-d]pyridazine-8-ylacetic acid.

DETAILED DESCRIPTION OF THE INVENTION

In accordance with the process employed for preparing the novel compounds of this invention, an appropriately substituted pyrido-pyridazinone acetic acid lower alkyl ester (having an available unsubstituted ring-nitrogen atom) of the formula:

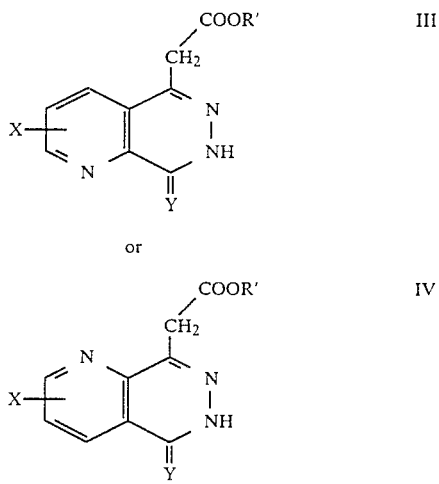

wherein X and Y are each as previously defined and R' is $C_1$-$C_6$ alkyl (and is preferably tertiary-butyl), is reacted with the appropriate aralkyl or heteroaralkyl halide of choice having the formula HalRCHWZ, where R, W (including R and W when taken together) and Z are each as previously defined in the structural formulae I and II for the final products and Hal is either chlorine, bromine or iodine. This reaction is normally carried out in the presence of a basic condensing agent such as an alkali metal hydride, alkanolate or amide, or an alkali metal-alkyl aryl (e.g., phenyl) compound and is usually conducted in a reaction-inert polar organic solvent, preferably using a cyclic ether such as dioxane and tetrahydrofuran or a cyclic amide such as N-methylpyrrolidone or one of the N,N-di- (lower alkyl) lower alkanoamides. Preferred solvents specifically include such solvents as dioxane and N,N-dimethylformamide. In general, substantially equimolar amounts of reactant and reagent are employed (i.e., from about 0.80 to about 1.25 mole of halide reagent with respect to the unsubstituted pyrido-pyridazinone acetic acid ester starting material) and the reaction is effected at a temperature that is in the range of from about 5° C. up to about 80° C. for a period of about seven up to about 64 hours. The reaction is usually conducted at room temperature (ca. 20° C.) for a period of time that is ordinarily at least about two and preferably about 16 hours. The reaction pressure is not critical for these purposes and, in general, the reaction will be carried out at a pressure that is in the range of from about 0.5 to about 2.0 atmospheres, and preferably at about ambient pressure (i.e., at about one atmosphere). The basic condensing agents required for the reaction are all selected from the class of alkali metal bases, previously enumerated, which are sufficiently strong to form salts with the weakly acidic unsubstituted pyrido-pyridazinone acetic acid ester and yet mild enough not to degrade the organic molecule under the conditions of the reaction. Such basic condensing agents include, for example, sodium hydride, lithium hydride and potassium hydride, etc., as well as sodium and potassium lower alkanolates like sodium methylate and potassium tert.-butoxide, as well as alkali metal amides like sodamide, lithium amide, potassium amide and so on. Upon completion of the reaction, the desired pyrido-pyridazinone acetic acid alkyl esters are readily recovered from the reaction mixture by the use of standard techniques well-known to those skilled in the art, e.g., the reaction mixture may be first diluted with ice water and then acidified with dilute aqueous acid, whereupon the desired pyrido-pyridazinone ester final product readily crystallizes out or at least precipitates from said acidified aqueous solution. Further purification can then be achieved, if so desired, by means of column chromatography over silica gel, preferably employing methylene chloride/ethyl acetate (1:1 by volume) as the eluent.

Conversion of the lower alkyl pyrido-pyridazinone acetic acid esters, prepared as described above, to the corresponding free acid final products of the present invention is then readily accomplished in a most convenient manner, viz., by effecting hydrolysis via the classical acid-catalyzed route, preferably using concentrated sulfuric acid or trifluoroacetic acid at temperatures ranging from below to about room temperature. In general, the acid-catalyzed hydrolysis reaction is effected at any temperature ranging from about 5° C. up to about 30° C. for a period of about five minutes to about six hours. Upon completion of the reaction, the desired pyrido-pyridazinone acetic acid final product is then easily isolated from the reaction mixture by standard procedure, such as, for example, by filtration of the precipitated product so obtained, followed by extraction with a base and then reacidification with a mineral acid to yield the desired acid compound in pure final form. Further purification of the latter material, if necessary, can then be effected by means of recrystallization from a suitable solvent, preferably using a lower alkanol such as ethanol or a lower alkanoic acid ester like ethyl acetate.

Compounds of the invention wherein Z of structural formula I or II is hydroxyphenyl can be readily prepared from the corresponding compounds where Z is methoxyphenyl by simply dealkylating same in accordance with standard techniques well known to those skilled in the art. For instance, the use of boron tribromide readily converts 6-benzyl-5-oxo-6H-pyrido[2,3-d]pyridazine-8-ylacetic acid compounds (of structural formula II) having a methoxy group at the paraposition on the phenyl moiety to the corresponding p-hydroxy compounds. Moreover, certain compounds of the invention of structural formula I where Z is alkoxyphenyl and said ring-substituent is lower alkoxy of more than one carbon atom can alternatively be prepared from the corresponding methoxy compounds by first converting same to the corresponding hydroxy derivatives and then alkylating the latter with, for example, ethyl iodide or isopropyl bromide in a manner well known to those skilled in the art.

As previously indicated, the pyrido-pyridazinone acetic acid final Products of structural formulae I and II can be used as such for the therapeutic purposes of this invention or else they can simply be converted to the corresponding lower alkyl ($C_1$-$C_6$) ester derivatives thereof in accordance with conventional techniques. The lower alkyl esters of the pyrido-pyridazinone acetic acids of this invention are generally prepared by condensation of the acid with the appropriate alcohol in the presence of an acid catalyst in accordance with conventional organic procedure. This method offers a facile route to those esters which are not readily obtained in the main process step.

The unsubstituted pyrido-pyridazinone acetic acid ester starting materials (of structural formulae III and IV) required for preparing the 6-substituted-5-oxo-6H-pyrido[2,3-d]pyridazine-8-ylacetic acids esters and 7-substituted-8-oxo-7H-pyrido[2,3-d]pyridazine-5-ylacetic acid esters (of structural formulae I and II) in the first process step of this invention are all new compounds which are prepared by (1) reacting the known 2,3-pyridinedicarboxylic acid anhydrides with the appropriate (alkoxycarbonylmethylene)triphenylphosporane compound to yield a mixture consisting essentially of the corresponding 3-oxo-pyrido[3,2-e]furan-1-ylidene acetic acid alkyl esters and the 3-oxo-pyrido[2,3-c]furan-1-ylidene acetic acid alkyl esters, followed by (2) chromatographic separation of the latter mixture into its component parts (viz., the aforesaid esters) and thereafter (3) reacting said separated esters with hydrazine hydrate, in accordance with the conventional methods of organic synthesis, to form the desired starting materials. These three reaction steps are hereinafter described in detail in the experimental section of the instant specification (see Preparations A–C).

The chemical bases which are used as reagents in this invention to prepare the aforementioned pharmaceutically acceptable base salts are those which form non-toxic base salts with the herein described pyrido-pyridazinone acetic acid compounds such as 6-(5-fluorobenzothiazole-2-ylmethyl)-5-oxo-6H-pyrido[2,3-d]pyridazine-8-ylacetic acid, for example. These non-toxic base salts include those derived from such pharmacologically acceptable cations as sodium, potassium, calcium and magnesium, etc. These salts can easily be prepared by simply treating the aforementioned pyrido-pyridazinone acetic acid compounds with an aqueous solution of the desired pharmacologically acceptable cation, and then evaporating the resulting solution to dryness, preferably under reduced pressure. Alternatively, they may be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

As previously indicated, the pyrido-pyridazinone acetic acid compounds of this invention are quite useful as aldose reductase inhibitors for the control of chronic diabetic complications, in view of their ability to effectively lower sorbitol levels in both the sciatic nerve and lens of various diabetic subjects. The herein described compounds of structural formulae I and II of this invention can be administered by either the oral, topical or parenteral routes of administration. In general, these compounds are most desirably administered in dosages ranging from about 0.5 mg. to about 25 mg. per kg. of body weight per day, although variations will necessarily occur depending upon the weight and condition of the subject being treated and the particular route of administration chosen.

These compounds may be administered either alone or in combination with pharmaceutically acceptable carriers by any of the routes previously indicated, and such administration can be carried out in either single or multiple dosages. More particularly, the compounds of this invention can be administered in a wide variety of different dosage forms, i.e., they may be combined with various pharmaceutically-acceptable inert carriers in the form of tablets, capsules, lozenges, troches, hard candies, powders, sprays, aqueous suspensions, injectable solutions, elixirs, syrups, and the like. Such carriers include solid diluents or fillers, sterile aqueous media and various non-toxic organic solvents. In general, the compounds of the invention will be present in such dosage forms at concentration levels ranging from about 0.5% to about 90% by weight of the total composition to provide the desired unit dosage.

For oral administration, tablets containing various excipients such as sodium citrate, calcium carbonate and calcium phosphate may be employed along with various disintegrants such as starch and preferably potato or tapioca starch, alginic acid and certain complex silicates, together with binding agents such as polyvinylpyrrolidone, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection would also include the high molecular weight polyethylene glycols. Where aqueous suspensions and/or elixirs are desired for oral administration, the essential active ingredient therein may be combined with various sweetening or flavoring agents, coloring matter or dyes, and if so desired emulsifying and/or suspending agents as well, together with such diluents as water, ethanol, propylene, glycol, glycerin and various combinations thereof.

For parenteral administration, solutions of these pyrido-pyridazinone acetic acid compounds (including the esters) in sesame or peanut oil or in aqueous propylene glycol or N,N-dimethylformamide may be employed, as well as sterile aqueous solutions of the corresponding water-soluble, alkali metal or alkaline-earth metal salts previously enumerated. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal injection. In this connection, the sterile aqueous media employed are all readily obtainable by standard techniques well-known to those skilled in the art. Additionally, it is also possible to administer the aforesaid pyrido-pyridazinone acetic acid compounds topically via an appropriate ophthamic solution (0.5–2.0%) applied dropwise to the eye.

The activity of the compounds of the present invention, as agents for the control of chronic diabetic complications, is determined by their ability to successfully pass one or more of the following standard biological or pharmacological tests, viz., (1) measuring their ability to inhibit the enzyme activity of isolated aldose reductase; (2) measuring their ability to reduce or inhibit sorbitol accumulation in the sciatic nerve of acutely streptozotocinized (i.e., diabetic) rats; (3) measuring their ability to reverse already-elevated sorbitol levels in the sciatic nerve and lens of chronic streptozotocin-induced diabetic rats; (4) measuring their ability to prevent: or inhibit galactitol formation in the lens of acutely galactosemic rats, and (5) measuring their ability to delay cataract formation and reduce the severity of lens opacities in chronic galactosemic rats.

PREPARATION A

A mixture consisting of 29.8 g. (0.200 mole) of commercially available 2,3-pyridinedicarboxylic acid anhydride and 75.2 g. (0.200 mole) of (tert.-butoxycarbonylmethylene)triphenylphosphorane in 1000 ml. of methylene chloride was stirred at room temperature (ca. 20° C.) for a period of 60 hours. Upon completion of this step, the resulting reaction mixture was evaporated to near dryness while under reduced pressure and the residue so obtained was thereafter chromatographed over 2.0 kg. of silica gel, followed by elution with a 49:1 (by volume) solution of methylene chloride in ethyl acetate. The separate eluent fractions were then carefully monitored by means of thin layer chromatography, and two different products were ultimately isolated.

The less polar product (yield, 2.09 g.) was designated as product (A) and identified as a mixture (1:1 by weight) of E- or Z-3-oxopyrido[2,3-c]furan-1-ylideneacetic acid tert.-butyl ester [$^1$H-NMR(CDCl$_3$, 250 MHz) 1.5(s, 9H), 6.1(s, 1H), 7.8(dd, J=6Hz, 1H), 8.40(dd, $J_1$=6Hz, $J_2$=1Hz, 1H), 9.1(dd, $J_1$=6H, $J_2$=1H, 1H)] and E-3-oxopyrido[3,2-c]furan-1-ylideneacetic acid tert.-butyl ester [$^1$H-NMR(CDCl$_3$, 250 MHz) 1.5(s, 9H), 6.2(s, 1H), 7.9(dd, J=6Hz, 1H), 9.0(dd, $J_1$=6Hz, 1H), 9.2(d, J=12Hz, 1H)]. This particular product was not separated into the pure components.

The molar polar product (yield, 14.1 g.) was designated as product (B) and identified as a mixture (ca. 1:10 by weight) of E-3-oxopyrido[3,2-c]furan-1-ylideneacetic acid tert.-butyl ester and Z-3-oxopyrido[2,3-c]furan-1-ylideneacetic acid tert.-butyl ester. This particular product was then further purified by being rechromatographed over 500 g. of silica gel, followed by elution with a 9:1 (by volume) solution of methylene chloride in ethyl acetate. Evaporation of the early eluent fractions while under reduced pressure then gave 1.89 g. (4%) of pure E-3-oxo-pyrido[3,2-c]furan-1-ylideneacetic acid tert.-butyl ester, m.p. 113°–114° C. Evaporation of the later fractions obtained in this manner then gave 11.5 g (23%) of pure E- or Z-3-oxopyrido[2,3-c]furan-1-ylideneacetic acid tert.-butyl ester, m.p. 118° C.

PREPARATION B

To a stirred solution consisting of 10 g. (0.04 mole) of E- or Z-3-oxopyrido[2,3-c]furan-1-ylideneacetic acid tert.-butyl ester (the product of Preparation A melting at 118° C.) dissolved in 25 ml. of ethanol, there were added 10 ml. of hydrazine hydrate in a dropwise manner and the resulting solution was then refluxed for a period of ten minutes. Upon completion of this step, the reaction mixture was next concentrated in vacuo to remove the ethanol solvent and the liquid residue subsequently obtained was diluted with 20 ml. of water, followed by the addition of sufficient 10% aqueous hydrochloric acid to adjust the final pH of the aqueous solution to a value of ca. pH 6.0. The precipitated solid product obtained in this manner was then collected by means of suction filtration and subsequently air-dried to constant weight to ultimately afford 8.9 g. (95%) of pure tert.-butyl 5-oxo-6H-pyrido[2,3-d]pyridazine-8-yl acetate, m.p. 178°–179° C.

PREPARATION C

To a stirred solution consisting of 1.85 g. (0.0075 mole) of E-3-oxopyrido[3,2-c]furan-1-ylideneacetic acid tert.-butyl ester (the product of Preparation A melting at 113°–114° C.) dissolved in 10 ml. of ethanol, there were cautiously added 1.3 ml. of hydrazine hydrate and the resulting solution was then gently refluxed for a period of one hour. Upon completion of this step, the reaction mixture was next concentrated in vacuo to remove the ethanol solvent and the liquid residue subsequently obtained was diluted with 20 ml. of water, followed by the addition of sufficient 10% aqueous hydrochloric acid to adjust the final pH of the solution to a value of ca. pH 2.0. The precipitated solid product obtained in this manner was then collected by means of suction filtration and subsequently air-dried to constant weight to ultimately afford 1.36 g. (69%) of pure tert.-butyl 8-oxo-7H-pyrido[2,3-d]pyridazine-5-yl acetate, m.p. 186°–188° C.

EXAMPLE 1

To a stirred solution consisting of 500 mg. (0.002 mole) of tert.-butyl 5-oxo-6H-pyrido[2,3-d]pyridazine-8-yl acetate (the product of Preparation B) dissolved in 5.0 ml. of N,N-dimethylformamide containing 250 mg. (0.0022 mole) of potassium tert.-butoxide, there was added 550 mg. (0.0022 mole) of 2-chloromethyl-5-trifluoromethylbenzothiazole at room temperature (ca. 20° C.) and the resulting reaction solution was thereafter stirred at that point for a period of ca. 16 hours (i.e., overnight). Upon completion of this step, the stirred reaction mixture was then poured over 20 ml. of ice-water, followed by the addition of sufficient 10% aqueous hydrochloric acid thereto so as to adjust the pH of the final aqueous solution to a value of ca. pH 5.0. The precipitated crude solid product obtained in this manner was then collected by means of suction filtration and further purified by means of chromatography over silica gel, using a 1:1 (by volume) mixture of methylene chloride and ethyl acetate as the eluent. In this way, there was ultimately obtained 660 mg. (69%) of pure tert.-butyl 6-(5-trifluoromethylbenzothiazole -2-ylmethyl)-5-oxo-6H-pyrido[2,3-d]pyridazine-8-yl acetate, m.p. 121°–122° C.

EXAMPLE 2

The procedure described in Example 1 was repeated except that 2-chloromethyl-5-fluorobenzothiazole was the reactant employed in place of 2-chloromethyl-5-trifluoromethylbenzothiazole, using the same molar proportions as before. In this particular case, the corresponding final product obtained was tert.-butyl 6-(5-fluorobenzothiazole-2-ylmethyl)-5-oxo-6H-pyrido[2,3-d]pyridazine-8-yl acetate; $^1$H-NMR(CDCl$_3$, 250 MHz) 1.4(s, 9H), 4.05(s, 2H), 5.8(s, 2H), 7.1(m, 1H), 7.7(m, 2H), 8.7(m, 1H), 9.1(m, 1H).

EXAMPLE 3

The procedure described in Example 1 was repeated except that 2-chloromethyl-5,7-difluorobenzothiazole was the reactant employed in place of 2-chloromethyl-5-trifluoromethylbenzothiazole, using the same molar proportions as before. In this particular case, the corresponding final product obtained was tert.-butyl 6-(5,7-difluorobenzothiazole-2-ylmethyl) -5-oxo-6H-pyrido[2,3-d]pyridazine-8-yl acetate, m.p. 139° C.

EXAMPLE 4

The procedure described in Example 1 was repeated except that 5-bromo-2-bromomethylbenzoxazole was the reactant employed in place of 2-chloromethyl-5-trifluomethylbenzothiazole, using the same molar proportions as before. In this particular case, the corresponding final product obtained was tert.-butyl 6-(5-bromobenzoxazole-2-ylmethyl)-5-oxo-6H-pyrido[2,3-d]pyridazine-8-yl acetate; 1H-NMR(CDCl₃, 250 MHz) 1.4(s, 9H), 4.0(s, 2H), 5.65(s, 2H), 7.3–7.5(m, 2H), 7.65(m, 1H), 7.8 (d, J=4Hz, 1H), 8.7(m, 1H), 9.1(m, 1H). The yield of pure product amounted to 85% of the theoretical value.

EXAMPLE 5

The procedure described in Example 1 was repeated except that 4-chloro-2-chloromethylbenzothiophene was the reactant employed in place of 2-chloromethyl-5-trifluoromethylbenzothiazole, using the same molar proportions as before. In this particular case, the corresponding final product obtained was tert.-butyl 6-(4-chlorobenzothiophene-2-ylmethyl)-5-oxo-6H-pyrido[2,3-d]pyridazine-8-yl acetate, m.p. 45°–50° C. The yield of pure product amounted to 58% of the theoretical value.

EXAMPLE 6

The procedure described in Example 1 was repeated except that 3-chloromethyl-5-(2-trifluoromethylphenyl)-1,2,4-oxadiazole was the reactant employed in place of 2-chloromethyl-5-trifluoromethylbenzothiazole, using the same molar proportions as before. In this particular case, the corresponding final product obtained was tert.-butyl 6-[5-(2-trifluoromethylphenyl)-1,2,4-oxadiazole-3-ylmethyl]-5-oxo-6H-pyrido[2,3-d]pyridazine-8-yl acetate, m.p. 90°–92° C. The yield of pure product amounted to 51% of the theoretical value.

EXAMPLE 7

The procedure described in Example 1 was repeated except that 4-bromo-2-fluorobenzyl bromide was the reactant employed in place of 2-chloromethyl-5-trifluoromethylbenzothiazole, using the same molar proportions as before. In this particular case, the corresponding final product obtained was tert.-butyl 6-(4-bromo-2-fluorobenzyl)-5-oxo-6H-pyrido[2,3-d]pyridazine-8-yl acetate, m.p. 117°–119° C. The yield of pure product amounted to 95% of the theoretical value.

EXAMPLE 8

To a stirred solution consisting of 630 mg. (0.0024 mole) of tert.-butyl 8-oxo-7H-pyrido,[2,3-d]pyridazine-5-yl acetate (the product of Preparation C) dissolved in 15 ml of N,N-dimethylformamide containing 310 mg. (0.0038 mole) of potassium tert.-butoxide, there was added 800 mg. (0.0028 mole) of 4-bromo-2-fluorobenzyl bromide at room temperature (ca. 20° C.) and the resulting reaction solution was thereafter stirred at that point for a period of about one hour. Upon completion of this step, the stirred reaction mixture was then poured over 50 ml. of ice-water, followed by the addition of aqueous hydrochloric acid thereto so as to adjust the pH of the final aqeous solution to a value of ca. pH 2.0. The precipitated crude solid product obtained in this manner was then collected by means of suction filtration (yield, 1.0 g.) and further purified by means of chromatography over silica gel, using a 1:1 (by volume) mixture of methylene chloride and ethyl acetate as the eluent. In this way, there was ultimately obtained 600 mg. (55%) of pure tert.-butyl 7-(4-bromo-2-fluorobenzyl)-8-oxo-7H-pyrido[2,3-d]pyridazine-5-yl acetate, m.p. 121°–122° C.

EXAMPLE 9

The procedure described in Example 8 was repeated except that 2-chloromethyl-5-trifluoromethylbenzothiazole was the reactant employed in place of 4-bromo-2-fluorobenzyl bromide, using the same molar proportions as before. In this particular case, the corresponding final product obtained was tert.-butyl 7-(5-trifluoromethylbenzothiazole-2-ylmethyl)-8-oxo-7H-pyrido[2,3-d]pyridazine-5-yl acetate, m.p. 124° C. The yield of pure product amounted to 49% of the theoretical value.

EXAMPLE 10

The procedure described in Example 8 is repeated except that 2-chloromethyl-5-fluorobenzothiazole is the reactant employed in place of 4-bromo-2-fluorobenzyl bromide, using the same molar proportions as before. In this particular case, the corresponding final product obtained is tert.-butyl 7-(5-fluorobenzothiazole-2-ylmethyl)-8-oxo-7H-pyrido[2,3-d]pyridazine-5-yl acetate.

EXAMPLE 11

The procedure described in Example 8 is repeated except that 2-chloromethyl-5,7-difluorobenzothiazole is the reactant employed in place of 4-bromo-2-fluorobenzyl bromide, using the same molar proportions as before. In this particular case, the corresponding final product obtained is tert.-butyl 7-(5,7-difluorobenzothiazole-2-ylmethyl)-8-oxo-7H-pyrido[2,3-d]pyridazine-5-yl acetate.

EXAMPLE 12

The procedure described in Example 8 is repeated except that 2-bromo-2-bromomethylbenzoxazole is the reactant employed in place of 4-bromo-2-fluorobenzyl bromide, using the same molar proportions as before. In this particular case, the corresponding final product obtained is tert.-butyl 7-(5,7-bromobenzoxazole-2-ylmethyl)-8-oxo-7H-pyrido[2,3-d]pyridazine-5-yl acetate.

EXAMPLE 13

The procedure described in Example 8 is repeated except that 4-chloro-2-chloromethylbenzothiophene is the reactant employed in place of 4-bromo-2-fluorobenzyl bromide, using the same molar proportions as before. In this particular case, the corresponding final product obtained is tert.-butyl 7-(4-chlorobenzothiophene-2-ylmethyl)-8-oxo-7H-pyrido[2,3-d]pyridazine-5-yl acetate.

EXAMPLE 14

The procedure described in Example 8 is repeated except that 2-chloromethyl-4-(2-trifluoromethylphenyl)imidazole is the reactant employed in place of 4-bromo-2-fluorobenzyl bromide, using the same molar proportions as before. In this particular case, the corresponding final product obtained is tert.-butyl 7-[4-(2-trifluoromethylphenyl)imidazole-2-ylmethyl]-8-oxo-7H-pyrido[2,3-d]pyridazine-5-yl acetate.

EXAMPLE 15

A solution consisting of 660 mg. (0.0014 mole) of tert.-butyl 6-(5-trifluoromethylbenzothiazole-2-ylmethyl)-5-oxo-6H-pyrido[2,3-d]pyridazine-8-yl acetate (the product of Example 1) dissolved in 2.0 ml. of ice-cold concentrated sulfuric acid was stirred at room temperature (ca. 20° C.) for a period of five minutes and then quenched with 10 ml. of ice-water. The resulting solid precipitate which formed at this point was then collected by means of suction filtration and subsequently extracted with 10% aqueous sodium bicarbonate solution. After washing the basic aqueous extract with two-separate 5.0 ml. portions of diethyl ether, the purified aqueous solution was then acidified to pH 2.0 with 10% aqueous hydrochloric acid to give a precipitate. The solid product so obtained was then recovered by means of suction filtration and thereafter crystallized from ethyl acetate to yield 310 mg. (53%) of pure 6-(5-trifluoromethylbenzothiazole-2-ylmethyl) -5-oxo-6H-pyrido[2,3-d]pyridazine-8-ylacetic acid, m.p. 168°–169° C.

EXAMPLE 16

The procedure described in Example 15 was repeated except that tert.-butyl 6-(5-fluorobenzothiazole-2-ylmethyl) -5-oxo-6H-pyrido[2,3-d]pyridazine-8-yl acetate (the product of Example 2) was the starting material employed in place of tert.-butyl 6-(5-trifluoromethylbenzothiazole-2-ylmethyl)-5-oxo-6H-pyrido[2,3-d]pyridazine-8-yl acetate, using the same molar proportions as before. In this particular case, the corresponding final product obtained was 6-(5-fluorobenzothiazole-2-ylmethyl)-5-oxo-6H-pyrido[2,3-d]pyridazine-8-ylacetic acid, m.p. 219° C. The yield of pure product amounted to 28% of the theoretical value.

EXAMPLE 17

The procedure described in Example 15 was repeated except that tert.-butyl 6-(5,7-difluorobenzothiazole-2-ylmethyl)-5-oxo-6H-pyrido[2,3-d]pyridazine-8-yl acetate (the product of Example 3) was the starting material employed in place of tert.-butyl 6-(5,7-difluorobenzothiazole-2-ylmethyl)-5-oxo-6H-pyrido2,3-d]pyridazine-8-yl acetate using the same molar proportions as before. In this particular case, the corresponding final product obtained was 6-5,7-difluorobenzothiazole-2-ylmethyl)-5-oxo-6H-pyrido[2,3-d]pyridazine-8-ylacetic acid, m.p. 196°–197° C. The yield of pure product amounted to 27% of the theoretical value.

EXAMPLE 18

The procedure described in Example 15 was repeated except that tert.-butyl 6-(5-bromobenzoxazole-2-ylmethyl)-5-oxo-6H-pyrido[2,3-d]pyridazine-8-yl acetate (the product of Example 4) was the starting material employed in place of tert.-butyl 6-(5-trifluorobenzothiazole-2-ylmethyl)-5-oxo-6H-pyrido-[2,3-d]pyridazine-8-yl acetate, using the same molar proportions as before. In this particular case, the corresponding final product obtained was 6-(5-bromobenzoxazole-2-ylmethyl)-5-oxo-6H-pyrido[2,3-d]pyridazine-8-ylacetic acid, m.p. 218° C.

EXAMPLE 19

The procedure described in Example 15 was repeated except that tert.-butyl 6-(4-chlorobenzothiophene-2-ylmethyl)-5-oxo-6H-pyrido[2,3-d]pyridazine-5-yl acetate (the product of Example 5) was the starting material employed in place of tert.-butyl 6-(5-trifluoromethylbenzothiazole-2-ylmethyl)-5-oxo-6H-pyrido-[2,3-d]pyridazine-8-yl acetate, using the same molar proportions as before. In this particular case, the corresponding final product obtained was 6-(4-chlorobenzothiophene-2-ylmethyl)-5-oxo-6H-pyrido[2,3-d]pyridazine-8-ylacetic acid, m.p. 169°–171° C. The yield of pure product amounted to 40% of the theoretical value.

EXAMPLE 20

The procedure described in Example 15 was repeated except that tert.-butyl 6-[5-(2-trifluoromethylphenyl)-1,2,4-oxadiazole-3-ylmethyl)-5-oxo-6H-pyrido[2,3-d]pyridazine-8-yl acetate (the product of Example 6) was the starting material employed in place of tert.-butyl 6-(5-trifluoromethylbenzothiazole-2-ylmethyl)-5-oxo-6H-pyrido-[2,3-d]pyridazine-8-yl acetate, using the same molar proportions as before. In this particular case, the corresponding final product obtained was 6-[5-(2-trifluoromethylphenyl)-1,2,4-oxadiazole-3-ylmethyl]-5-oxo-6H-pyrido[2,3-d]pyridazine-8-ylacetic acid, m.p. 240° C. The yield of pure product amounted to 41% of the theoretical value.

EXAMPLE 21

The procedure described in Example 15 was repeated except that tert.-butyl 6-(4-bromo-2-fluorobenzyl)-5-oxo-6H-pyrido[2,3-d]pyridazine-8-yl acetate (the product of Example 7) was the starting material employed in place of tert.-butyl 6-(5-trifluoromethylbenzothiazole-2-ylmethyl)-5-oxo-6H-pyrido-[2,3-d]pyridazine-8-yl acetate, using the same molar proportions as before. In this particular case, the corresponding final product obtained was 6-(4-bromo-2-fluorobenzyl)-5-oxo-6H-pyrido[2,3-d]pyridazine-8-ylacetic acid, m.p. 194°–195° C. The yield of pure product amounted to 26% of the theoretical value.

EXAMPLE 22

The procedure described in Example 15 was repeated except that 500 mg. (0.0011 mole) of tert.-butyl 7-(4-bromo-2-fluorobenzyl)-8-oxo-7H-pyrido[2,3-d]pyridazine-5-yl acetate (the product of Example 8) was the starting material employed in place of 600 mg. of tert.-butyl 6-(5-trifluoromethylbenzothiazole-2-ylmethyl)-5-oxo-6H-pyrido-[2,3-d]pyridazine-8-ylacetate, using the same molar proportions as before. In this particular case, there was ultimately obtained 400 mg. (93%) of pure 7-(4-bromo-2-fluorobenzyl)-8-oxo-6H-pyrido[2,3-d]pyridazine-5-ylacetic acid (m.p. 198° C.) after one crystallization from ethanol.

EXAMPLE 23

The procedure described in Example 15 is repeated except that tert.-butyl 7-(5-trifluoromethylbenzothiazole-2-ylmethyl))-8-oxo-7H-pyrido[2,3-d]pyridazine-5-yl acetate (the product of Example 9) was the starting material employed in place of tert.-butyl 6-(5-trifluoromethylbenzothiazole-2-ylmethyl)-5-oxo-6H-pyrido[2,3-d]pyridazine-8-yl acetate, using the same molar proportions as before. In this particular case, the corresponding final product obtained is 7-(5-trifluoromethylbenzothiazole-2-ylmethyl)-8-oxo-7H-pyrido[2,3-d]pyridazine-5-ylacetic acid.

EXAMPLE 24

The procedure described in Example 15 is repeated except that tert.-butyl 7-(5-fluorobenzothiazole-2-ylmethyl)-8-oxo-7H-pyrido[2,3-d]pyridazine-5-yl acetate (the product of Example 10) is the starting material employed in place of tert.-butyl 6-(5-trifluoromethylbenzothiazole-2-ylmethyl)-5-oxo-6H-pyrido-[2,3-d]pyridazine-8-yl acetate, using the same molar proportions as before. In this particular case, the corresponding final product obtained is 7-(5-fluorobenzothiazole-2-ylmethyl)-8-oxo-7H-pyrido[2,3-d]pyridazine-5-ylacetic acid.

EXAMPLE 25

The procedure described in Example 15 is repeated except that tert.-butyl 7-(5,7-difluorobenzothiazole-2-methyl)-8-oxo-7H-pyrido[2,3-d]pyridazine-5-yl acetate (the product of Example 11) is the starting material employed in place of tert.-butyl 6-(5-trifluoromethyl-benzothiazole-2-ylmethyl)-5-oxo-6H-pyrido-[2,3-d]pyridazine-8-yl acetate, using the same molar proportions as before. In this particular case, the corresponding final product obtained is 7-(5,7-difluorobenzothiazole-2-ylmethyl)-8-oxo-7H-pyrido[2,3-d]pyridazine-5-ylacetic acid.

EXAMPLE 26

The procedure described in Example 15 is repeated except that tert.-butyl 7-(5-bromoxazole-2-ylmethyl)-8-oxo-7H-pyrido[2,3-d]pyridazine-5-yl acetate (the product of Example 12) is the starting material employed in place of tert.-butyl 6-(5-trifluoromethylbenzothiazole-2-ylmethyl)-5-oxo-6H-pyrido-[2,3-d]pyridazine-8-yl acetate, using the same molar proportions as before. In this particular case, the corresponding final product obtained is 7-(5-bromoxazole-2-yl-methyl)-8-oxo-7H-pyrido[2,3-d]pyridazine-5-ylacetic acid.

EXAMPLE 27

The procedure described in Example 15 is repeated except that tert.-butyl 7-(4-chlorobenzothiophene-2-methyl)-8-oxo-7H-pyrido[2,3-d]pyridazine-5-yl acetate (the product of Example 13) is the starting material employed in place of tert.-butyl 6-(5-trifluoromethyl-benzothiazole-2-ylmethyl)-5-oxo-6H-pyrido-[2,3-d]pyridazine-8-yl acetate, using the same molar proportions as before. In this particular case, the corresponding final product obtained is 7-(4-chlorobenzothiophene-2-ylmethyl)-8-oxo-7H-pyrido[2,3-d]pyridazine-5-ylacetic acid.

EXAMPLE 28

The procedure described in Example 15 is repeated except that tert.-butyl 7-[4-(2-trifluoromethylphenyl)imidazole-2-ylmethyl]-8-oxo-7H-pyrido[2,3-d]pyridazine -5-yl acetate (the product of Example 14) is the starting material employed in place of tert.-butyl 6-(5-trifluoromethylbenzothiazole-2-ylmethyl)-5-oxo-6H-pyrido[2,3-d]pyridazine-8-yl acetate, using the same molar proportions as before. In this particular case, the corresponding final product obtained is 7-[4-(2-trifluoromethylphenyl)imidazole-2-ylmethyl]-8-oxo-7H-pyrido[2,3-d]pyridazine-8-ylacetic acid.

EXAMPLE 29

The following pyrido-pyridazinone acetic acid compounds of Examples 15–21, respectively, were tested for their ability to reduce or inhibit aldose reductase enzyme activity via the procedure of S. Hayman et al., as described in the *Journal of Biological Chemistry*, Vol. 240, p. 877 (1965) and as modified by K. Sestanj et al. in U.S. Pat. No. 3,821,383. In every case, the substrate employed was partially purified aldose reductase enzyme obtained from human placenta. The results obtained with each compound are expressed below in terms of their percent inhibition of enzyme activity (%) with respect to the various concentration levels tested:

| Compound | Percent Inhibition (%) | | |
| --- | --- | --- | --- |
| | $10^{-5}$ M | $10^{-6}$ M | $10^{-7}$ M |
| Product of Example 15 | 88 | 81 | 74 |
| Product of Example 16 | 94 | 91 | 90 |
| Product of Example 17 | 75 | 65 | 39 |
| Product of Example 18 | 93 | 87 | 31 |
| Product of Example 19 | 80 | 60 | 8 |
| Product of Example 20 | 77 | 72 | 43 |
| Product of Example 21 | 86 | 76 | 30 |

We claim:
1. A compound of the formula:

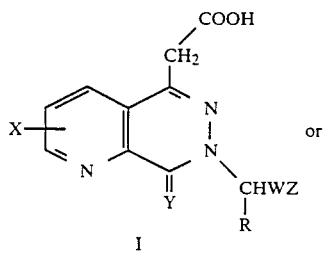

or

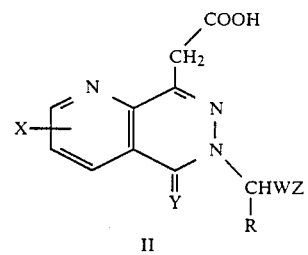

or a $C_1$–$C_6$ alkyl ester thereof, or a base salt of said formula I or II acid with a pharmacologically acceptable cation, wherein R is hydrogen or methyl;

W is —(CH$_2$)— wherein n is zero or one; or

R and W, when taken together with the central carbon atom to which they are attached to form RCHW, complete a vinylene group;

X is hydrogen, fluorine, chlorine, bromine, trifluoromethyl, $C_1$–$C_4$ alkyl, $C_1$–$C_4$ alkoxy or $C_1$–C alkylthio;

Y is oxygen or sulfur; and

Z is phenyl, benzothiophen-2-yl, benzoxazol-2yl, benzothiazol-2-yl or phenyl-1,2,4-oxadiazol-3-yl, wherein said phenyl, benzothiophenyl, benzoxazolyl, benzothiazolyl and phenyloxadiazolyl groups are each optionally monosubstituted or disubstituted on the benzene ring, the substituents for monosubstitution being selected from fluorine, chlorine, bromine, trifluoromethyl, $C_1$–$C_4$ alkyl, $C_1$–$C_4$ alkoxy and hydroxy and the substituents for disubstitution being identical or non-identical, with said identical substituents being selected from fluorine, chlorine, bromine, trifluoromethyl, $C_1$–$C_4$ alkyl and $C_1$–$C_4$ alkoxy and said non-identical substituents being selected from fluorine, chlorine, bromine, trifluoromethyl, methyl, methoxy and hydroxy.

2. A compound as claimed in claim 1 of the formula I.

3. A compound as claimed in claim 1 of the formula II.

4. A compound as claimed in claim 1 of the formula I wherein R and X are each hydrogen, Y is oxygen, W is —$(CH_2)_n$— wherein n is zero and Z is substituted phenyl.

5. A compound as claimed in claim 4 wherein Z is 4-bromo-2-fluorophenyl.

6. A compound as claimed in claim 1 of the formula II wherein R and X are each hydrogen, Y is oxygen, W is —$(CH_2)_n$— wherein n is zero and Z is substituted phenyl-1,2,4-oxadiazol-3-yl.

7. A compound as claimed in claim 6 wherein Z is 5-(2-trifluoromethylphenyl)-1,2,4-oxadiazol-3-yl.

8. A compound as claimed in claim 1 of the formula II wherein R and X are each hydrogen, Y is oxygen, W is —$(CH_2)_n$— wherein n is zero and Z is substituted phenyl.

9. A compound as claimed in claim 8 wherein Z is 4-bromo-2-fluorophenyl.

10. A compound as claimed in claim 1 of the formula II wherein R and X are each hydrogen, Y is oxygen, W is —$(CH_2)_n$— wherein n is zero and Z is substituted benzothiophen-2-yl.

11. A compound as claimed in claim 10 wherein Z is 4-chloro-2-benzothiophen-2-yl.

12. A compound as claimed in claim 1 of the formula II wherein R and X are each hydrogen, Y is oxygen, W is —$(CH_2)_n$— wherein n is zero and Z is substituted benzoxazol-2-yl.

13. A compound as claimed in claim 12 wherein Z is 5-bromobenzoxazol-2-yl.

14. A compound as claimed in claim 1 of the formula II wherein R and X are each hydrogen, Y is oxygen, W is —$(CH_2)_n$— wherein n is zero and Z is substituted benzothiazol-2-yl.

15. A compound as claimed in claim 14 wherein Z is 5-fluorobenzothiazol-2-yl.

16. A compound as claimed in claim 14 wherein Z is 5,7-difluorobenzothiazol-2-yl.

17. A compound as claimed in claim 14 wherein Z is 5-trifluoromethylbenzothiazol-2-yl.

18. A compound as claimed in claim 1 which is a $C_1$–$C_6$ alkyl ester.

19. A compound as claimed in claim 18 which is a tertiary-butyl ester.

20. A pharmaceutical composition useful for preventing or alleviating chronic complications in a diabetic subject, said composition comprising a pharmaceutically-acceptable inert carrier as the diluent and as the essential active therein a compound as claimed in claim 1 in an amount effective for the treatment of said diabetes-associated chronic complications.

21. A method for treating a diabetic subject to prevent or alleviate chronic complications arising in said subject, which comprises administering to said diabetic subject an effective therapeutic amount of a compound as claimed in claim 1.

22. A compound of the formula:

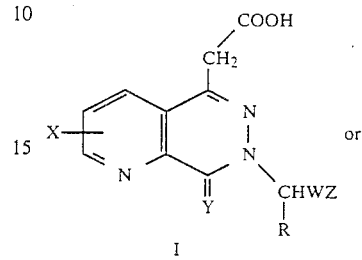

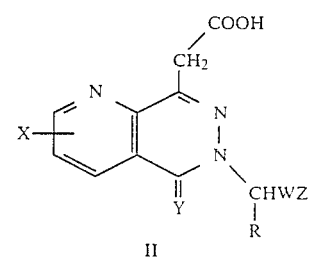

or a $C_1$–$C_6$ alkyl ester thereof, or a base salt of said formula I or II acid with a pharmacologically acceptable cation, wherein R is hydrogen or methyl;

W is —$(CH_2)_n$— wherein n is zero or one; or

R and W, when taken together with the central carbon atom to which they are attached to form RCHW, complete a vinylene group;

X is hydrogen, fluorine, chlorine, bromine, trifluoromethyl, $C_1$–$C_4$ alkyl, $C_1$–$C_4$ alkoxy or $C_1$–$C_4$ alkylthio;

Y is oxygen or sulfur; and

Z is phenyl, optionally monosubstituted or disubstituted, the substituents for monosubstitution being selected from fluorine, chlorine, bromine, trifluoromethyl, $C_1$–$C_4$ alkyl and hydroxy and the substituents for disubstitution being identical or non-identical, with said identical substituents being selected from fluorine, chlorine, bromine, trifluoromethyl, $C_1$–$C_4$ alkyl and $C_1$–$C_4$ alkoxy and said non-identical substituents being selected from fluorine, chlorine, bromine, trifluoromethyl, methyl, methoxy and hydroxy.

* * * * *